United States Patent [19]

Howard, III et al.

[11] Patent Number: 4,869,247

[45] Date of Patent: Sep. 26, 1989

[54] VIDEO TUMOR FIGHTING SYSTEM

[75] Inventors: Matthew A. Howard, III; Rogers C. Ritter; Grady, M. Sean, all of Charlottesville, Va.

[73] Assignee: The University of Virginia Alumni Patents Foundation, Charlottesville, Va.

[21] Appl. No.: 167,217

[22] Filed: Mar. 11, 1988

[51] Int. Cl.$^4$ .............................................. A61B 17/36
[52] U.S. Cl. .................... 128/303.1; 600/12
[58] Field of Search ....................... 600/10–13; 128/804, 303.1, 401, 422

[56] References Cited

U.S. PATENT DOCUMENTS

| | | | |
|---|---|---|---|
| 3,358,676 | 12/1967 | Frei et al. | 600/12 |
| 3,626,940 | 12/1971 | Zaffaroni | 128/1.3 X |
| 3,653,385 | 4/1972 | Burton | 600/10 X |
| 4,013,063 | 3/1977 | Bucalo | 128/1 R |
| 4,136,683 | 1/1979 | Gordon | 128/736 |
| 4,186,729 | 2/1980 | Harrison | 128/1.3 X |
| 4,269,826 | 5/2981 | Zimmerman et al. | 600/12 X |
| 4,323,056 | 4/1982 | Borelli et al. | 128/1.3 |
| 4,340,038 | 7/1982 | McKean | 128/1.3 |
| 4,364,377 | 12/1982 | Smith | 600/12 |
| 4,434,341 | 2/1984 | Busby | 219/10.55 A |
| 4,690,130 | 9/1987 | Mirell | 600/10 X |

FOREIGN PATENT DOCUMENTS 281869 10/1913 Fed. Rep. of Germany .
1284528 12/1968 Fed. Rep. of Germany ... 128/303.1

OTHER PUBLICATIONS

Thackray et al., "Indirect heating . . . Tumor" Electrocomp. Sci. & Tech., vol. 1, No. 2, pp. 91–96, 12/1974 (copy 1258/422).

"Observations of the Use of Ferromagnetic Implants for Inducing Hyperthermia", Paul R. Stauffer et al., IEEE Transactions on Biomedical Engineering, vol. BME-31, No. 1 (Jan. 1984).

Primary Examiner—Lee S. Cohen
Attorney, Agent, or Firm—James Creighton Wray

[57] ABSTRACT

A destructive heat lesion is placed in any location in the brain. A patient's head is secured within a stereotactic frame. After a high resolution CT scan and angiogram or MRI, data is incorporated and analyzed by a computer. This information is then resynthesized and projected as a video image on a screen facing the surgeon. A small magnetic object, perhaps a ball, is inserted into the patient's head via a burr hole drilled through the patient's skull. Using, real time fluoroscopic data superimposed on the computer image of three-dimensional structures, the surgeon is able to control and manipulate the object through the patient's soft brain tissue to a position next to or inside of the tumor area. An energy beam is then fired at the object, causing the more heat efficient object to destroy the brain tumor area. This procedure is repeated until the entire tumor is eradicated by the highly localized hyperthermia. The above procedure can be used to deliver hyperthermia, chemotherapy, radiotherapy and other agents or treatments to the brain and other parts of the body as well.

33 Claims, 4 Drawing Sheets

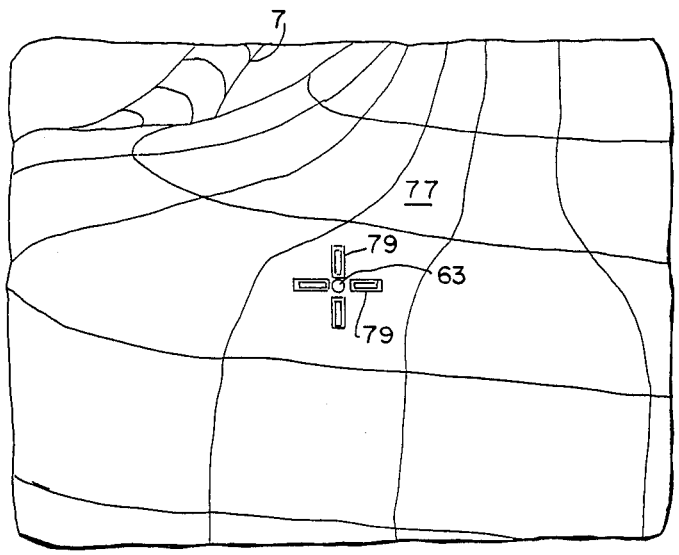
FIG. 3
FIG. 4
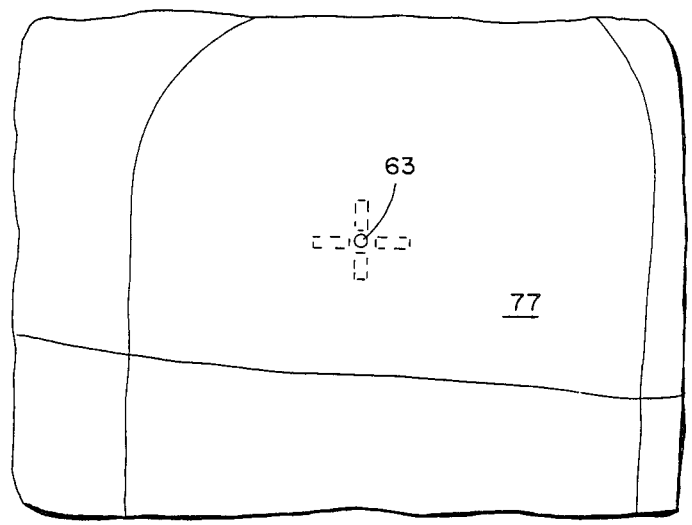
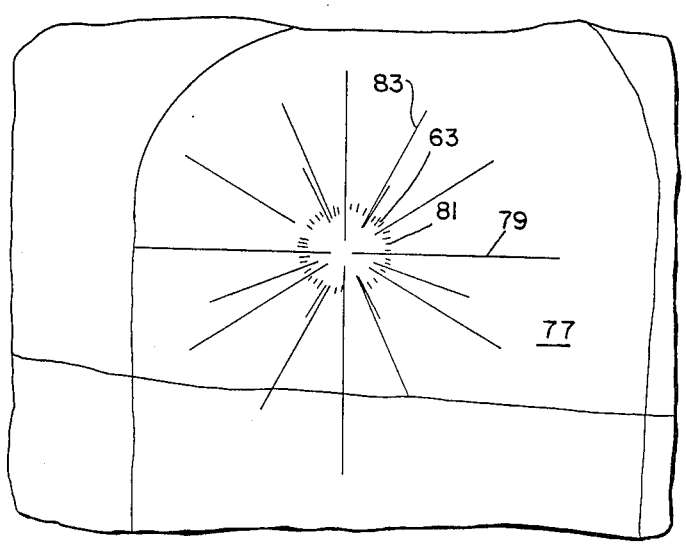
FIG. 5

VIDEO TUMOR FIGHTING SYSTEM

BACKGROUND OF THE INVENTION

Conventional neurosurgery is limited in its ability to treat deep seated tumors because of the necessity of cutting through normal brain and vasculature to obtain access to the tumor. Radiation therapy carries with it the problems of high dose ionizing radiation which is both destructive to normal tissue and like chemotherapy oftentimes ineffective in stopping tumor growth.

A fast growing malignancy deep inside the brain is difficult to treat because existing surgical procedures require cutting through or otherwise damaging normal brain structures. In general, both the patient's post-operative condition and his prognosis for recovery are often poor. Partly because of this, a research area has sprung up in which generalized hyperthermia, introduced by radio-frequency irradiation of the tumor's region, is used in an attempt to kill the tumor cells. If there were some way of sufficiently localizing hyperthermia to the tumor itself, hyperthermia could be a much more effective adjuvant or primary treatment method for brain tumors. The present invention provides such a method.

SUMMARY OF THE INVENTION

A destructive stereotactic heat lesion is placed precisely in any location in the brain without significant damage to surrounding areas. Incorporating principles of physics, computer science and neuroanatomy, this system enables neurosurgeons to safely destroy pathologic lesions, while sparing normal brain tissue.

The advantages of this system are several.

Previously in accessible brain tumors are safely destroyed without cutting through and damaging eloquent areas of brain.

All brain tumors, regardless of their location, are destroyed with much greater precision and less damage to surrounding brain.

Subsequent procedures to treat residual tumors that may have been missed the first time can be performed with less difficulty than the first procedure.

Subsequent procedures to treat residual tumors that may have been missed the first time can be performed with much less difficulty than with other treatment methods.

No materal tether for guidance or pushing rod for emplacement is necessary.

The procedure maybe performed under local anesthesia with the heat lesion destroying the tumor. Operative morbidity and mortality are decreased.

Ionizing radiation is not used as a destructive force.

The side effects of chemotherapy can be avoided.

The potential damage of generalized hyperthermia is avoided.

This device has a broad range of surgical applications in addition to destroying tumors.

The present invention is an entirely new and revolutionary approach to destroying brain tumors. There are two fundamental principles of physics incorporated into this system. The first involves suspension and/or manipulation of a small magnetic object in space using an electromagnet. This technology is currently available and has the capacity to move and position a object in space with less than 1 mm error. It has been found that the brain's soft composition enables a small ball or other object to be moved through it in this fashion.

The second part of this invention entails directing an energy beam, for example a radio frequency electromagnetic wave, which is preferentially absorbed by the suspended object. Because of the difference in atomic composition between the object and brain tissue, the object absorbs the energy as heat much more efficiently than brain tissue. Only a discrete area of tissue surrounding the heated object is destroyed. Our studies in directing electromagnetic energy at particles embedded in mammalian brains have proved this principle.

Either of two methods are employed individually in a variety of clinical applications. The preferred application involves computer integration of the methods, taking advantage of advanced imaging techniques to produce a precision video tumor fighter. This system operates as follows:

The patient's head is secured within a stereotactic frame. High resolution CT scan and angiogram or MRI (magnetic resonance imaging) studies are then performed. Data is incorporated and analyzed by computer. Three dimensional coordinates occupied by vascular structures, tumor, or eloquent area of brain are recorded. The eloquent areas of brain are defined previously using a conventional stereotactic atlas and programming these loci into the software. This information is then resynthesized and projected as a vidio image on a screen facing the surgeon. This image recreates the spatial relationship between the position of the object and the previously mentioned areas of importance in a form that can be understood by the surgeon and enables him to avoid zones of danger and minimize damage as he makes his approach to the tumor. This technique of computer imaging of three dimensional structures for the purpose of avoiding zones of danger as used in advanced attack aircraft is adaptable to the video tumor fighter.

After imaging is complete, an incision is made through the scalp, a burr hole is drilled, dura reflected and the object is placed on the exposed brain. The surgeon takes his position at the controls facing the video screen. The magnet is positioned and activated. Using an appropriate real time imaging method in conjunction with the previously stored imaging data, the surgeon avoids danger zones as he pilots the object into the tumor. Once the object is within the tumor, the energy beam is fired at the object. The object is heated, and it destroys a small area of surrounding tissue. This loss can be projected on the screen as a defect in the tumor image, the size of which is dependent on the energy setting of the beam and the length of fire time. The object is further advanced into the tumor, the energy beam is fired again, perhaps this time from a slightly different angle, still energizing the object, but passing through a different line or normal brain tissue to avoid excessive exposure of one tract of tissue. This procedure is repeated until the entire tumor is eradicated. Finally, the object is left suspended within the brain for further use or the computer directs the object back to the burr hole, or the surgeon carefully pilots the object back to the burr hole. If desired, the object is removed and the skin closed.

These and other and further objects and features of the invention are apparent in the disclosure, which includes the above and ongoing description, drawings and claims.

BRIEF DESCRIPTION OF THE DRAWINGS

FIG. 3 shows a screen schematic when a surgeon has advanced the ball and is now closing in on the tumor.

FIG. 4 shows a screen schematic with the ball advanced into the substance of the tumor.

FIG. 5 shows a screen when an energy beam is fired into the ball.

DETAILED DESCRIPTION OF THE DRAWINGS

Figure 1:
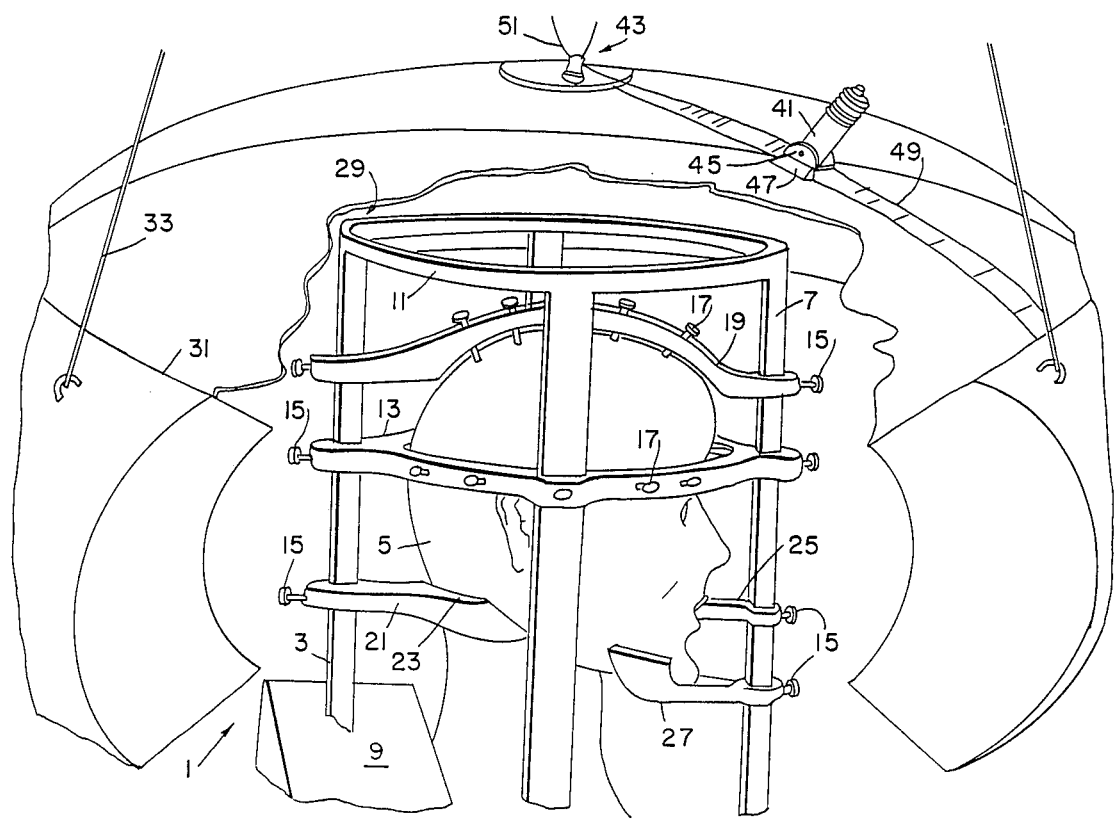
FIG. 1 is a schematic representation of a patient's head positioned in stereotactic head frame. An electromagnet device with an energy beam generator are shown in place.

Referring to FIG. 1, a video tumor fighter of the present invention is generally indicated by the numeral 1. A frame 3 surrounds a patient's head 5 and holds the head in fixed position relative to the frame. The frame 3 has longitudinal members 7 which may be anchored in fixed structure 9. A circular member 11 is joined to the longitudinal members 7. A moveable central circular member 13 has adjustment screws 15 for holding the central member at a fixed position and has skull or scalp contacting screws 17 for contacting the skull or scalp of the patient.

An upper skull bridging member 19 has similar adjusting and contacting screws 15 and 17. A lower member 21 is forked 23 to receive the base of the skull. An adjustment screw 15 holds the forked skull base member in fixed position. A mouthpiece is cantilevered on member 25, which is held in place by adjustment screw 15. A chin-supporting member 27 is also held in place by an adjusting screw 15. The entire stereotactic frame device, which is generally indicated by the numeral 29, is made of suitable material. During the CAT-scan and MRI procedure, the position of the skull with respect to the headframe is sensed and is recorded in the computer-stored data.

Surrounding the stereotactic headframe is an electromagnet device 31 shown cutaway, which is suspended on cables 33 from the ceiling or from an overhead frame. An energy beam generator 41 is positioned on an adjustable tracking device 43 which includes a hinge 45 and a slide 47 mounted on a track 49. A radial inward portion of track 49 is supported on a device 51, which is in turn supported from the ceiling or from an overhead frame. The device may be used in any orientation, although a vertical orientation is shown in the drawing. The patient's skull is placed or maintained in the identical position in the headframe during the surgical procedure. A small scalp flap is opened, and a small hole is drilled in the skull. A small magnetic object, such as a ball or a cylinder with rounded ends, is placed in the opening.

Figure 2:
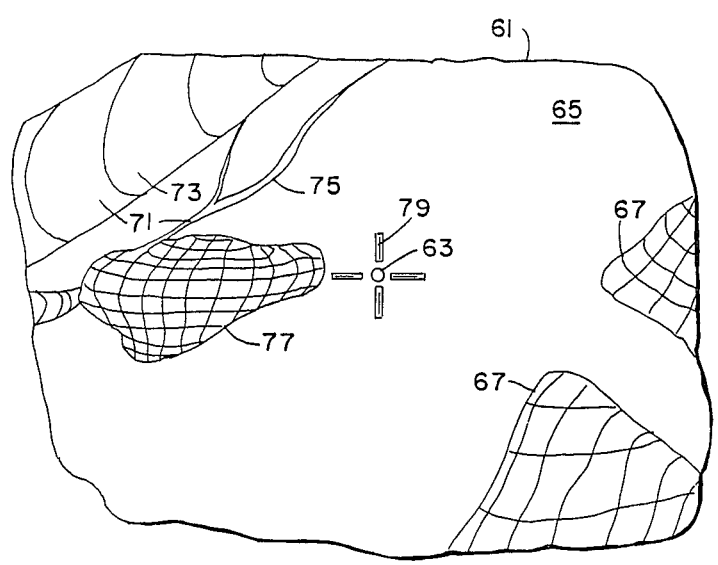
FIG. 2 shows a video display displaying 3-D coordinates of ball position within the brain. Cross hairs depict ball position relative to the tumor, eloquent brain, and vasculative tubular structures.

FIG. 2 shows a video display screen 61 which displays three-dimensional coordinates of a fluoroscopic image 63 of a object positioned with a computer-stored and reproduced image of the brain generally indicated by the numeral 65. Eloquent volumes of the brain 67, which are to be avoided, are displayed on the screen. Images from a double fluoroscopic unit are combined into a three-dimensional image within the computer. Using conventional techniques, the screen image may be shifted to effectively observe the brain, tumor and surgical object from any angle.

Vascular tubular structures 71, such as artery 73 and capillaries 75, are displayed. A three-dimensional image of a tumor 77 is also displayed. Cross-hairs 79 depict the object position relative to the tumor, to the eloquent brain volumes, and to the vacular tubular structures.

As shown in FIG. 3, as the image 63 of the object is advanced near the tumor 77. The cross-hairs 79 indicate the precise position of the object.

FIG. 4 depicts a larger scale on the screen, with the object image 63 advanced into the substance of tumor 77.

FIG. 5 shows an image of the screen as the energy beam is fired into the object, heating the object. The image shown on the screen shows an expanded image 81 of the heated object with fine cross-hairs 79 and radiating lines 83, together, which indicates heat penetration into the tumor 77. The enlarged heated volume may be displayed such as in a different color and may be stored in the computer memory to indicate a heat treated destroyed tumor portion. The object may be advanced, stopped, heated, and moved sequentially until the tumor is substantially or totally destroyed. Alternatively, the object may be continuously heated as it is moved within the tumor.

Figure 6:
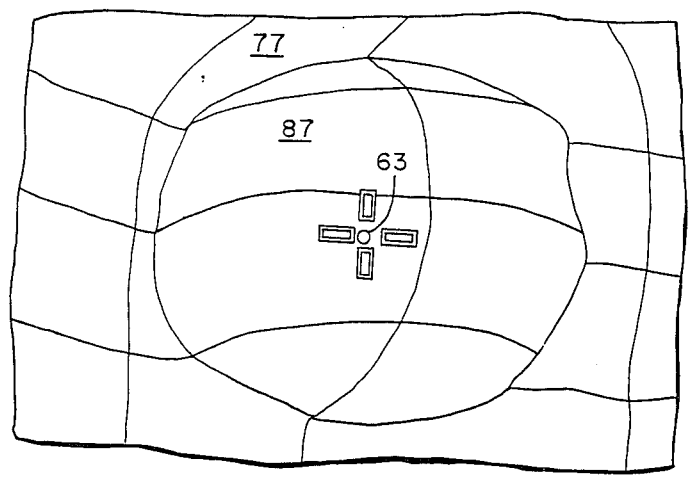
FIG. 6 shows a computer screen image of defect caused by the heated ball.

FIG. 6 shows the computer image of a defect or lesion 87 created in the tumor 77 as caused by the heated object 63.

Figure 7:
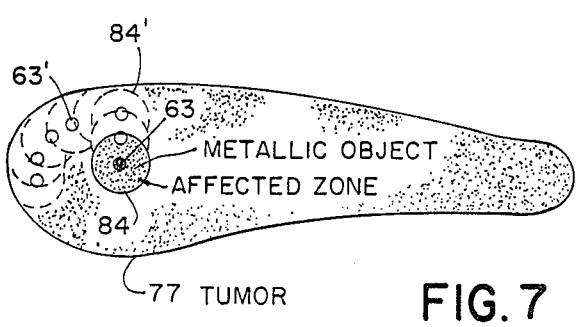
FIG. 7 is a schematic representation of a tumor within a brain and a metallic object within a tumor for focusing destructive energy therein and showing an affected zone around the metallic object.

FIG. 7 shows a schematic representation of a tumor 77 in which an energy receiving object 63 has been positioned. Irradiating the object 63 with energy has caused an expanded affected zone 84 around the object. As shown in the drawing the prior or intended path of the object 63 is indicated by the broken lines which are identified by 63'. The broken lines identified by 84' identify the affected zones from prior positioning of the object 63 or the zones which will be intended to be affected by subsequent positions of object 63.

Figure 8:
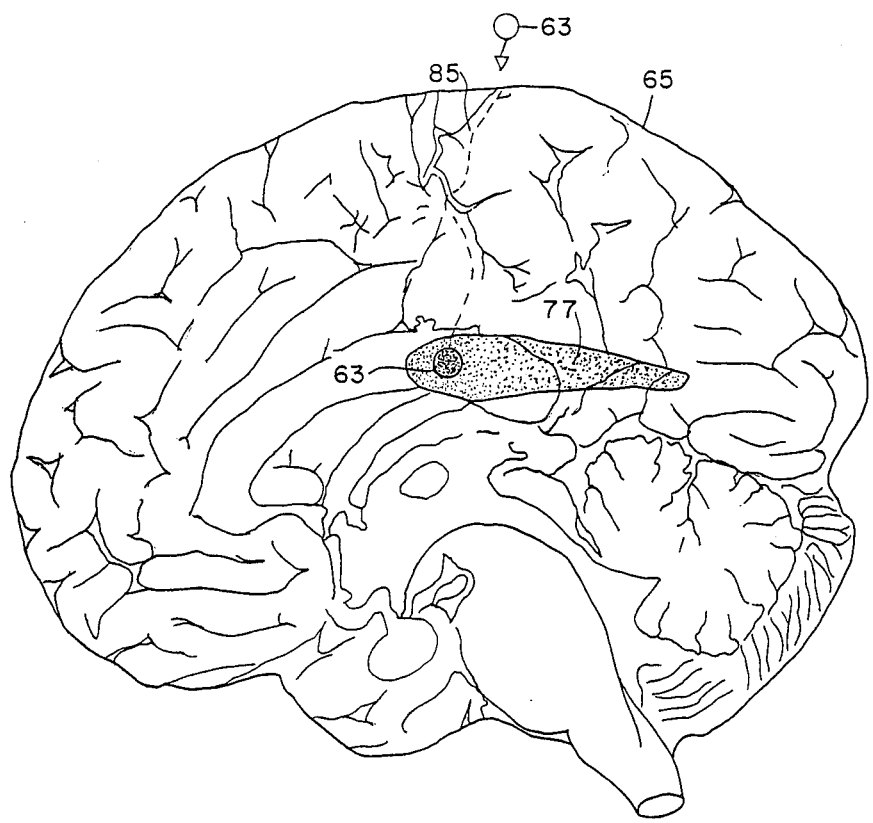
FIG. 8 is a schematic drawing of a brain showing a tumor in shaded form within a brain and an energy focusing object within the tumor together with a path by which the object has been inserted in the tumor.

FIG. 8 is a schematic representation of a brain 65 in which an object 63 has been steered into a tumor 77. The dotted line indicated by the numeral 85 indicates the path through which the object has been steered into the tumor 77. The dotted line indicated by the numeral 85 indicates the path through which the object has been steered into the tumor.

Figure 9:
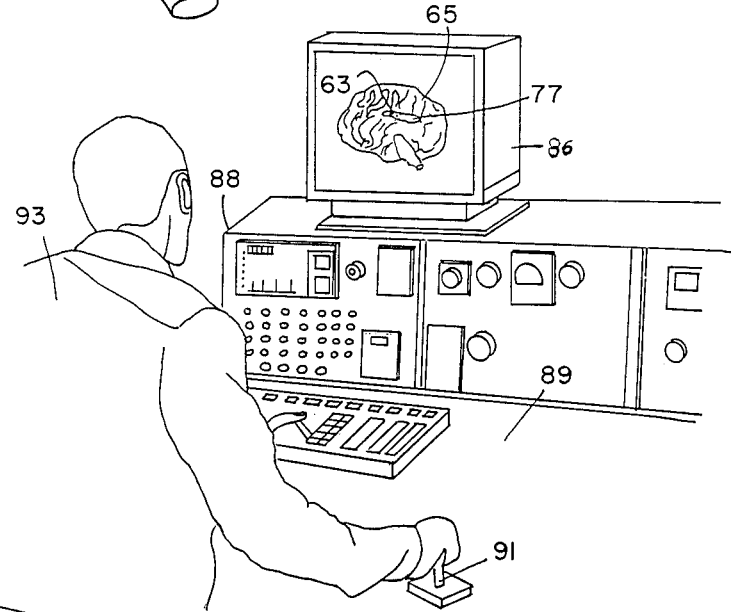
FIG. 9 is a schematic representation of a physician at a control console used for moving an object within a brain and guiding the object into a tumor and heating the object.

FIG. 9 shows the image of an object 63 within a tumor 77 in a brain 65 shown on display 86. A computer console 88 as controlled by terminal 89 and a guidance control 91 operated by a doctor 93 steers object 63 through the brain and heats the object with radio frequency energy beams.

The computer 88 is used to record physiological data of the brain from MRI and/or CT scans and angiograms and is used to store and reproduce that data to form the image 65 of the brain on the display and is used to correlate the real time imaging of the object 63 with the previously recorded data and to concurrently display the images.

Figure 10:
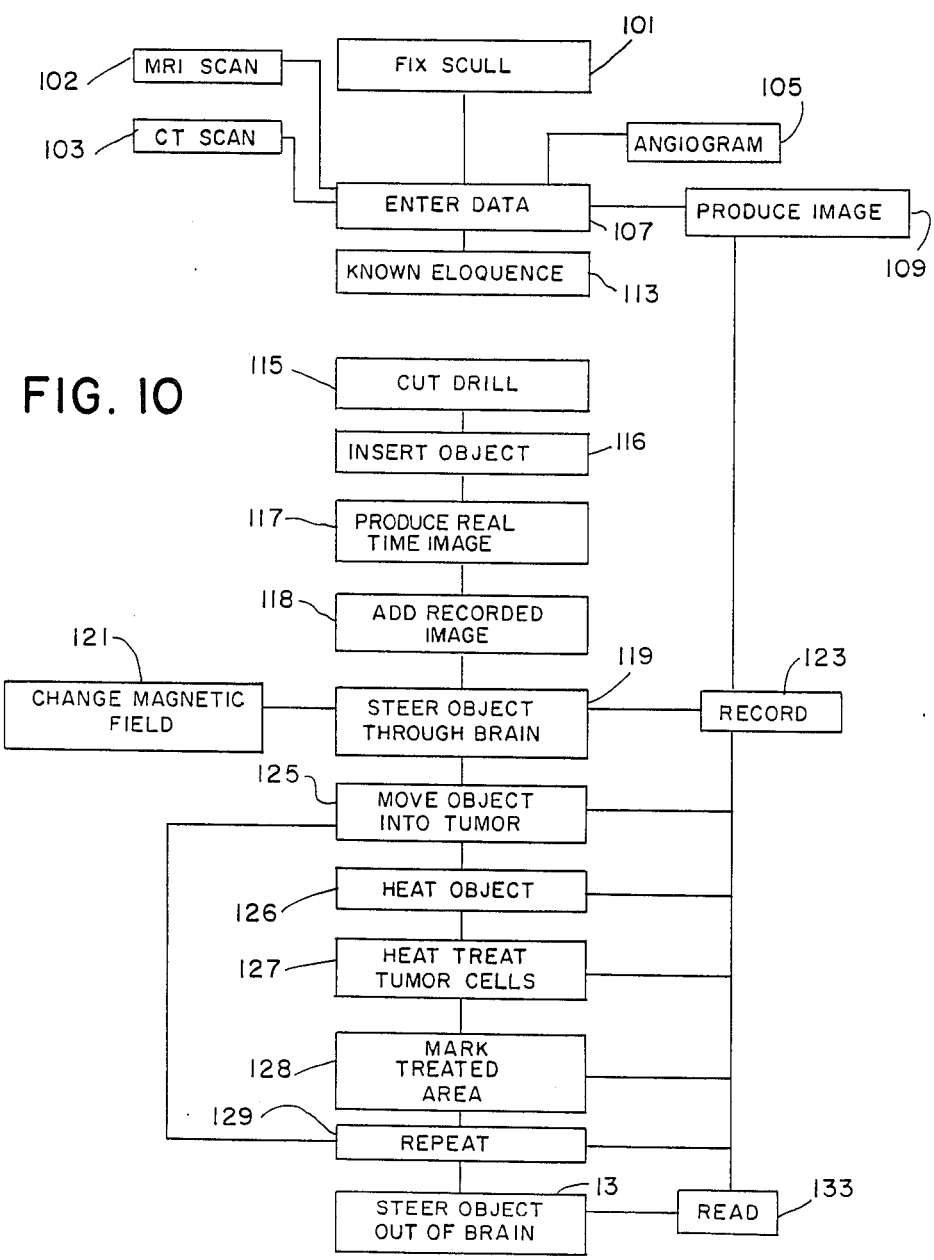
FIG. 10 shows a flowchart of steps needed to operate the video tumor fighter so as to destroy a tumor.

FIG. 10 is a flowchart of steps. The first step is to fix a patient's skull 101 in the stereotactic device. Then a CT scan 103 and MRI and/or an angiogram 105 are performed. Data is entered 107 in a computer, and an image is produced 109 on a screen 111. Known eloquent brain voumes 113 are entered in the computer and identified as distinct images on the screen. The patient's scalp is cut and the skull is drilled 115. An object is inserted 117 through the opening in the skull and the object is steered 119 through the brain by moving the magnet and/or by adjusting its strength. The steering of the object through the brain is recorded 123. The object is moved 125 into the tumor and is heated 127 until the surrounding tumor tissue dies. Steps 125 and 127 are repeated 129 and finally the object is left in the brain or is steered 131 out of the brain, such as along its entry path by data read 133 from the recorded data.

Preferably, a cooled or super conducting coil constitutes the electromagnet, which provides the magnetic field to manipulate the object. The magnet is moved around the stationary head frame to position the object within the brain. The object is any suitable object which has sufficient magnetic qualities to be manipulated within a brain by the field of the electromagnet. Larger objects are usually easier to manipulate. Permanent magnets of increased strength are usually easier to manipulate. Smaller objects are easier to move through a brain. Shape differences may promote energy absorption and/or movement. Objects may be coated with materials which promote radio frequency (rf) heating or conducting heat to surrounding tissue. Tumor cells are killed at slightly lower temperature than healthy brain cells. Temperatures appropriate to different vascularities, different tumor types and locations, different rates of object motion, and other factors may vary.

As an example, a patient's head is scanned and an image of a brain is produced and stored in a computer. An angiogram may be used to produce a display of and store data concerning vascular structure of the brain. A patient's skull is drilled and a small metallic object and about ⅛th of an inch in diameter is placed within the hole. The stored image of the patient's brain and the real time image of the metallic object are correlated by the computer and a physician uses computer controls to change position and strength of a magnet adjacent the patient's head to steer the metallic object through the brain. When the object appears on the display to be within the area of the previously recorded tumor, the physician energizes a radio frequency generator to direct a beam to the object and heat the object. The beam which for example may be a radio frequency beam extends through the patient's head and brain and excites the metallic object, causing it to heat. The radio frequency energy passes through the watery cells of the brain and the bone cells of the skull without causing damage to those healthy cells. The only change noted is the increased temperature of the object which is in its desired location.

Advantageously, the object may be heated to a temperature which is sufficient to destroy tumor cells immediately adjacent the object and for a zone surrounding the object. When the object is positioned deep within a tumor, it may be heated to a greater degree or for a longer time. When the object is positioned near the border of the tumor and healthy cells, it may be heated for a shorter time or to a lesser degree.

Many brain tumors are of a soft nature and can be penetrated by the object. In the event that a tumor cannot be penetrated by the object, the object may be moved along the tumor and heated to destroy or weaken peripheal tumor cells. Advantageously, if the tumor is not penetrable by the object, healthy cells surrounding the tumor may be destroyed or weakened to interrupt outward progress of the tumor.

As an example, a metallic object deep within a tumor may be heated to a temperature of up to about 150 degrees F. or more. An object near the interface of a tumor and healthy tissue may be heated to a temperature of about 110 degrees F., for example.

While the invention has been described with reference to specific embodiments, modifications and variations may be made without departing from the scope of the invention which is defined in the following claims.

We claim:

1. The method of cranial tumor treatment, comprising:
   (a) immobilizing a patient's head;
   (b) conducting a scan of the patient's head and obtaining data from the scan and inputting the data in a computer;
   (c) inputting data of vascular tubular brain structure and eloquent brain structure in the computer;
   (d) displaying three-dimensional images of the patient's brain, vascular tubular structures, eloquent brain regions and tumor;
   (e) opening a scalp of the patient and drilling an opening in a skull of the patient;
   (f) inserting a small magnetic object within the opening in the skull;
   (g) placing an electromagnet around the skull;
   (h) controlling movement of the object within the skull and brain by changing a magnetic field size and direction of the electromagnet and steering the movement of the object within the skull and brain to avoid eloquent regions of the brain and vascular tubular structures and guiding the object into contact with and into a position within the tumor;
   (i) positioning an energy beam generator on a tracking device adjacent to the skull;
   (j) moving the energy beam genertor into a position to direct energy to the object within the tumor;
   (k) energizing the energy beam generator and directing energy from the beam generator into the object;
   (l) heating the object with energy directed into the object from the energy beam generator;
   (m) creating a lesion within the tumor in a region surrounding the object by heat from the object;
   (n) moving the object into another zone of the tumor by changing the field with the electromagnet;
   (o) holding the object in a new position;
   (p) directing energy from the energy beam generator into the object in its new position;
   (q) creating a second lesion within the tumor by heat from the object and continuing the repositioning of the object within the tumor and energizing the energy beam generator and heating the object and creating lesions within regions of the tumor surrounding the object by heat from the object;

(r) guiding the object outward from the lesions and steering the object through the brain while avoiding the eloquent regions of the brain and the vascular tubular structures within the brain;

(s) directing the object to the opening in the skull;

(t) removing the object the from the skull through the opening;

(u) closing the opening in the skull; and (v) closing the opening in the scalp.

2. The method of claim 1 wherein the subsequent directing of energy from the energy beam generator is prefaced by relocating the energy beam generator to direct the energy beam through regions of the skull and brain through which energy beams have not previously been directed.

3. The method of claim 1 wherein the steering of the object out of the tumor and through the brain to the skull comprises steering the object through the same path in which the object was steered through the brain toward the tumor.

4. The method of claim 1 further comprising creating a real time image created by cross-secting fluoroscopic images and superimposing the real time image on a pre-determined image of the brain to facilitate guidance of the object.

5. The method of claim 1 wherein the object is moved continuously and is heated, simultaneously.

6. The method of brain tumor treatment comprising mounting a frame on a patient's head, scanning the brain and a tumor within the brain, obtaining data from the scanning and inputting the data into a computer, inputting data of vascular tubular brain structure and eloquent brain structure in the computer, displaying three-dimensional images of the patient's brain, vascular tubular structures, eloquent brain regions and tumors, opening a scalp of the patient and drilling an opening in a skull of the patient, inserting a small magnetic object within the opening in the skull, placing an electromagnet around the skull, supplying power to the electromagnet, cooling the electromagnet, moving the electromagnet outside of the skull, observing movement of the object within the brain, controlling movement of the object within the brain by moving the electromagnet and steering the movement of the object within the brain to avoid eloquent regions and vascular tubular structures of the brain and guiding the object into contact with and into a position within the tumor, positioning an energy beam generator adjacent to the skull, moving the energy beam generator to a position to direct energy to the object within the tumor, energizing the energy beam generator and directing energy from the beam generator to the object, heating the object with directed energy from the energy beam generator, creating a lesion within regions of the tumor surrounding the object by heat from the object, moving the object into another zone of the tumor by changing position of the electromagnet, holding the object in a new position, directing energy from the energy beam generator to the object in its new position, and creating a second lesion within the tumor by heat from the object, and continuing the repositioning of the object within the tumor and energizing the energy beam generator and heating the object and creating lesions within regions of the tumor surrounding the object by heat from the object, guiding the object outward from the lesions and steering the object through the brain while avoiding the eloquent regions of the brain and the vascular tubular structures within the brain, directing the object to the opening in the skull, and removing the object from the skull through the opening, closing the opening in the skull and closing the opening in the scalp.

7. The method of claim 6 wherein the subsequent directing of energy from the energy beam generator is preceded by relocating the energy beam generator to direct the energy beam through regions of the skull and brain through which energy beams have not previously been directed.

8. The method of claim 6 wherein the steering of the object out of the tumor and through the brain to the skull comprises steering the object through the same path in which the object was steered through the brain toward the tumor.

9. The method of claim 6 further comprising superimposing real time fluoroscopic images of the brain on a pre-determined image of the brain to facilitate guidance of the object.

10. The method of claim 6 wherein the object is moved continuously and is heated simultaneously, as necessary to obtain the desired effects.

11. The method treating a body part, comprising:
initially conducting a scan of the body part and storing data from the scan;
creating a computer screen image with the stored data;
inserting a magnetic object within the body part;
magnetically coupling the magnetic object to a magnetic field of an electromagnet;
observing the object within the body part by generating an image of the observed object and superimposing the generated image with a previous computer generated image of the body part;
moving the electromagnet outside of the body which moves the magnetic object within the body to a desired location according to the previously generated image and the superimposed generated image;
activating the magnetic object; and
delivering treatment utilizing the magnetic object to the desired location in the body.

12. The method of claim 11 wherein the delivering treatment in the desired location comprises delivering hyperthermia treatment in the desired location.

13. The method of claim 11 wherein the delivering treatment in the desired location comprises delivering chemotherapy in the desired location.

14. The method of claim 11 wherein the delivering of teatment in the desired location comprises delivering radiotherapy in the desired location.

15. The method of claim 11 wherein the magnetic object is moved continuously and is heated simultaneously, as necessary to obtain the desired effects.

16. The method of claim 15 further comprising leaving the object inside the body.

17. The method of claim 15 wherein the activating of the object comprises heating the object to destroy tissue immediately surrounding the object.

18. The method treating a body part, comprising:
initially conducting a scan of the body part and storing data from the scan;
creating a computer screen image with the stored data;
inserting a magnetic object within the body part;
magnetically coupling the magnetic object to a magnetic field of an electromagnet;
observing the object within the body part by generating an image of the observed object and superimposing the generated image with a previous computer generated image of the body part;
changing a magnetic field of the electromagnet which moves the magnetic object within the body to a desired location according to the previously generated image and the superimposed generated image;
activating the magnetic object; and
delivering treatment utilizing the magnetic object to the desired location.

19. The method of claim 18 wherein the delivering treatment in the desired location comprises delivering hyperthermia treatment in the desired location.

20. The method of claim 19 further comprising activating the object to treat non-neoplastic conditions that are known to benefit from ablative procedures.

21. The method of claim 18 wherein the delivering treatment in the desired location comprises delivering chemotherapy in the desired location.

22. The method of claim 18 wherein the delivering of treatment in the desired location comprises delivering radiotherapy in the desired location.

23. The method of claim 18 wherein the object is moved continuously and is heated, simultaneously for treating the body part.

24. The method of claim 18 wherein the object is left inside the body.

25. The method of claim 18 wherein the activating of the object comprises heating the object to destroy tissue immediately surrounding the object.

26. A video tumor fighting method comprising placing a destructive heat lesion in any location in the brain by first securing a patient's head within a stereotactic frame, scanning the patient's head with a high resolution CT scan and angiogram or magnetic resonance imaging, incorporating and analyzing data from the scanning in a computer, resynthesizing and projecting a computer video image of three dimensional structures on a screen facing a surgeon, drilling a hole through the patient's skull, inserting a magnetic object into the patient's head via the hole, generating real time fluoroscopic data, superimposing the real time data on the computer image of three-dimensional structures, controlling and manipulating the object through soft brain tissue of the patient to a position next to or inside of a lesion within the brain and treating the lesion with the object.

27. The method of claim 26, wherein the treatment in the lesion comprises activating the object by a high energy beam to deliver localized heating in the lesion.

28. The method of claim 26 wherein the treatment in the lesion comprises activating the object to cause hyperthermia in the lesion.

29. The method of claim 26 wherein the treatment in the lesion comprises activating the object to deliver chemotherapy in the lesion.

30. The method of claim 26 wherein the treatment in the lesion comprises activating the object to deliver radiotherapy in the lesion.

31. A video tumor fighter system comprising:
magnetic object means for inserting in a body part;
electromagnet means positioned outside of the body part for producing a magnetic field which captures the magnetic object means;
positioning means connected to the electromagnet means for moving the electromagnet means adjacent the body part, wherein the electromagnet means moves the magnetic object means within the body part to a desired location;
control means connected to the positioning means for controlling the positioning means' movement of the electromagnet means;
beam producing means for directing a beam into the body part to the magnetic object means, wherein the beam producing means is mounted adjacent the body part and has a firing means connected to the beam producing means for controlling the firing of the beam into the body part at the magnetic object means and wherein further the control means also controls the firing means; and
observing means for observing the magnetic object means within the body part.

32. The method of cranial tumor treatment, comprising:
(a) immobilizing a patient's head;
(b) conducting a scan of the patient's head and obtaining data from the scan and inputting the data in a computer;
(c) inputting data of vascular tubular brain structure and eloquent brain structure in the computer;
(d) displaying three-dimensional images of the patient's brain, vascular tubular structures, eloquent brain regions and tumor;
(e) opening a scalp of the patient and drilling an opening in a skull of the patient;
(f) inserting a small magnetic object within the opening in the skull;
(g) placing an electromagnet around the skull;
(h) controlling movement of the object within the skull and brain by changing a magnetic field size and direction of the electromagnet and steering the movement of the object within the skull and brain to avoid eloquent regions of the brain and vascular tubular structures and guiding the object into contact with and into a position within the tumor;
(i) positioning an energy beam generator on a tracing device adjacent to the skull;
(j) moving the energy beam generator into a position to direct energy to the object within the tumor;
(k) energizing the energy beam generator and directing energy from the beam generator into the object;
(l) heating the object with energy directed into the object from the energy beam generator;
(m) creating a lesion within the tumor in a region surrounding the object by heat from the object;
(n) moving the object into another zone of the tumor by changing the field with the electromagnet;
(o) holding the object in a new position;
(p) directing energy from the energy beam generator into the object in its new position;
(q) creating a second lesion within the tumor by heat from the object and continuing the repositioning of the object within the tumor and energizing the energy beam generator and heating the object and creating lesions within regions of the tumor surrounding the object by heat from the object;
(r) guiding the object outward from the lesions and steering the object to a suitable safe place within the brain and leaving it at that location;
(s) closing the opening in the skull; and
(t) closing the opening in the scalp.

33. The method of brain tumor treatment comprising mounting a frame on a patient's head, scanning the brain and a tumor within the brain, obtaining data from the scanning and inputting the data into a computer, inputting data of vascular tubular brain structure and eloquent brain structure in the computer, displaying three-dimensional images of the patient's brain, vascular tubular structures, eloquent brain regions and tumors, opening a scalp of the patient and drilling an opening in a skull of the patient, inserting a small magnetic object within the opening in the skull, placing an electromagnet around the skull, supplying power to the electromagnet, cooling the electromagnet, moving the electromagnet outside of the skull, observing movement of the object within the brain, controlling movement of the object within the brain by moving the electromagnet and steering the movement of the object within the brain to avoid eloquent regions and vascular tubular structures of the brain and guiding the object into contact with and into a position within the tumor, positioning an energy beam generator adjacent to the skull, moving the energy beam generator to a position to direct energy to the object within the tumor, energizing the energy beam generator and directing energy from the beam generator to the object, heating the object with directed energy from the energy beam generator, creating a lesion within regions of the tumor surrounding the object by heat from the object, moving the object into another zone of the tumor by changing position of the electromagnet, holding the object in a new position, directing energy from the energy beam generator to the object in its new position, and creating a second lesion within the tumor by heat from the object, and continuing the repositioning of the object within the tumor and energizing the energy beam generator and heating the object and creating lesions within regions of the tumor surrounding the object by heat from the object, guiding the object outward from the lesions to a suitably safe place within the brain and leaving it at that location, closing the opening in the skull and closing the opening in the scalp.

* * * * *